United States Patent [19]

Schulsinger et al.

[11] Patent Number: 5,925,510
[45] Date of Patent: Jul. 20, 1999

[54] MEDIUM FOR PRESERVING TISSUE WITHOUT TISSUE CULTURING OCCURRING

[75] Inventors: David A. Schulsinger, New York; Philip S. Li, Flushing; Marc Goldstein, New York, all of N.Y.

[73] Assignee: Cornell Research Foundation, Inc., Ithaca, N.Y.

[21] Appl. No.: 08/946,936

[22] Filed: Oct. 8, 1997

Related U.S. Application Data

[60] Provisional application No. 60/027,935, Oct. 11, 1996.

[51] Int. Cl.⁶ .................................................. A01N 1/02
[52] U.S. Cl. ............................................................ 435/1.1
[58] Field of Search ....................... 435/1.1, 240–240.24; 623/11

[56] References Cited

U.S. PATENT DOCUMENTS

| | | | |
|---|---|---|---|
| 4,673,649 | 6/1987 | Boyce et al. | 435/378 |
| 4,963,489 | 10/1990 | Naughton et al. | 435/240.1 |
| 5,032,508 | 7/1991 | Naughton et al. | 435/32 |
| 5,104,787 | 4/1992 | Lindstrom et al. | 435/1 |
| 5,166,048 | 11/1992 | Soll et al. | 435/1 |
| 5,407,669 | 4/1995 | Lindstrom et al. | 424/78.04 |
| 5,443,950 | 8/1995 | Naughton et al. | 435/1 |
| 5,512,475 | 4/1996 | Naughton et al. | 435/240.243 |
| 5,516,680 | 5/1996 | Naughton et al. | 435/240.243 |
| 5,516,681 | 5/1996 | Naughton et al. | 435/240.243 |
| 5,518,915 | 5/1996 | Naughton et al. | 435/240.243 |
| 5,747,341 | 5/1998 | Brothers | 435/404 |

OTHER PUBLICATIONS

Quinn, P., et al., Fertility and Sterility, vol. 44, No. 4, 493–498 (Oct. 1985).

*Primary Examiner*—Mickey Yu
*Assistant Examiner*—John M. Black

[57] ABSTRACT

A method for autotransplantation, is provided including the steps of (a) obtaining a piece of tissue from one part of a body, (b) preserving the tissue by contacting it with a tissue preserving medium, without tissue culturing occurring, and (c) grafting the tissue in another part of the body. The method is especially advantageous for the repair of hypospadias using buccal mucosa tissue. The tissue preserving medium preferably is a solution of (a) 80–120 mM NaCl, (b) 3–6 mM KCl, (c) 0.1–0.3 mM $MgSO_4 \cdot 7H_2O$, (d) 1–3 mM $CaCl_2 \cdot 2H_2O$, (e) 0.2–0.6 mM $NaH_2PO_4$, (f) 1.5–4 mM glucose, (g) 15–25 mM Na lactate, (h) 0.2–0.6 mM Na pyruvate, (i) 0.01–0.05 mM phenol red, (j) 0.1–0.4 mM L-glutamine, (k) 2–35 mM sodium bicarbonate, (l) 125–200 units/ml penicillin-G, (m) 40–60 μg/ml streptomycin sulfate, (n) vehicle consistent with tissue preservation; said medium having a pH ranging from 7.0–7.8.

5 Claims, No Drawings

MEDIUM FOR PRESERVING TISSUE WITHOUT TISSUE CULTURING OCCURRING

CROSS-REFERENCE TO RELATED APPLICATION

This application claims the benefit of Ser. No. 60/027,935, filed on Oct. 11, 1996.

TECHNICAL FIELD

The present invention relates to a medium for preserving tissue and to a method for autotransplantation utilizing medium for preserving tissue between the time of removal from the donor location and transplantation.

BACKGROUND OF THE INVENTION

Autotransplantation, i.e., the transfer of one's own tissue from one location to another, is used, for example, for replacement or repair in the urinary tract or in the vascular system or in other body sites.

In autotransplantations, one problem is preserving the tissue between the time of removal from the donor location and the transplantation so as to improve chances of effective transplantation.

We turn now to hypospadias. This is a well recognized urologic congenital anomaly occurring in one of three hundred newborn boys in which the urethral opening is on the underside of the penis at a point proximal to the distal end of the penis. In most instances, primary reconstruction can be accomplished with local penile and preputial skin. Occasionally, the pediatric urologist is confronted with the situation of deficient genital skin due to a prior operation or a high degree of urethral abnormality. In some instances, free extragenital non-hair bearing skin tissue, bladder mucosa tissue, and buccal mucosa tissue have been used as grafts for forming a urethra. The graft tissue is implanted into the penis to form a complete urethra. Urethrocutaneous fistulas are a persistent problem in hypospadias repair with an incidence up to 30%. A reason for the incidence of urethrocutaneous fistulas is believed to be inadequate preservation of the graft, especially where the graft is extragenital tissue.

SUMMARY OF THE INVENTION

The present invention provides a tissue preserving medium which is especially prepared for preserving tissue in autotransplantation and a method of autotransplantation where incidence of urethrocutaneous fistulas is reduced by the preservation of the tissue between the time it is removed from the donor location and the transplantation.

In one embodiment herein there is provided a medium for preserving tissue in autotransplantation (e.g., between the time it is removed from the donor location and transplantation). The medium is preferably in the form of a solution and consists essentially of the following composition:

80–120 mM NaCl
3–6 mM KCl
0.1–0.3 mM $MgSO_4.7H_2O$
1–3 mM $CaCl_2.2H_2O$
0.2–0.6 mM $NaH_2PO_4$
1.5–4 mM glucose
15–25 mM Na lactate
0.2–0.6 mM Na pyruvate
0.01–0.05 mM phenol red
0.1–0.4 mM L-glutamine
2–35 mM sodium bicarbonate
125–200 units/ml penicillin-G
40–60 μg/ml streptomycin sulfate
vehicle (consistent with tissue preservation)

and has a pH ranging from 7.0–7.8. The medium is to preserve the tissue without tissue culturing occurring. It functions as a nutrition medium.

In a second embodiment herein there is provided a method for autotransplantation comprising the steps of (a) obtaining a piece of tissue from one part of a body,
(b) preserving the piece of tissue by contacting it with a tissue preserving medium, without tissue culturing occurring,
(c) grafting the piece of tissue in another part of the same body.

DETAILED DESCRIPTION

We turn now to the embodiment of the tissue preserving medium in more detail.

Preferably the tissue preserving medium herein is buffered to a pH ranging from 7.0–7.8. Buffering is preferably provided by HEPES, i.e., N-(2-hydroxyethyl) piperazine-N'-2-ethanesulfonic acid. Other buffers include, for example, combinations of $KH_2PO_4$ and $Na_2HPO_4.2H_2O$, and tris buffer, i.e., 2-amino-2-hydroxymethyl-1,3-propanediol. Tissue, when disconnected and prior to grafting, undergoes anaerobic respiration, and the produced $CO_2$ causes the tissue to become more acid, and the acidity can lead to tissue death. The buffering reduces or eliminates the acidity effect so tissue is less likely to die.

The vehicle is preferably an aqueous vehicle and very preferably is selected from the group consisting of aqueous HEPES solution, Ringer's solution and saline. The water in the vehicle is preferably recently boiled distilled water. The most preferred vehicle is aqueous HEPES solution, preferably used so HEPES is present in the medium at a concentration of 10–25 mM.

The sodium bicarbonate ingredient is preferably sodium bicarbonate without protein, that is sodium bicarbonate that is free of protein.

The presence of two antibiotics including the presence of at least 125 units/ml penicillin-G, preferably at least 150 units/ml penicillin-G, mitigates the chance of infection occurring in the graft tissue after reconstruction is completed.

A preferred tissue preserving medium is an aqueous solution having the following composition:

102 mM NaCl
4.7 mM KCl
0.2 mM $MgSO_4.7H_2O$
2 mM $CaCl_2.2H_2O$
0.5 mM $NaH_2PO_4$
2.8 mM glucose
21 mM Na lactate
0.4 mM Na pyruvate
0.02 mM phenol red
0.2 mM L-glutamine
4 mM sodium bicarbonate
150 units/ml penicillin-G 50 μg/ml streptomycin sulfate 21 mM HEPES water The tissue preserving medium is readily made up by adding the ingredients in any order to water. For a buffered medium, the buffer is preferably the first ingredient added to the water vehicle when the medium is made from scratch. Alternatively, a commercial composition may be purchased consistent with the medium composition and modified by addition of ingredients as necessary.

The preferred tissue preserving medium described above should be stored at 4 to 5° C., has a shelf life of 60 days from the date of preparation and has been designated Pedic-Uro MHR™ medium.

We turn now in more detail to the second embodiment herein.

In said second embodiment there is provided a method for autotransplantation comprising obtaining a piece of tissue from one part of a body; preserving the tissue, without tissue culturing occurring, in a tissue preserving medium, e.g., at a pH of 7.0 to 7.8; and then grafting the tissue in another part of the same body. The use of the tissue preserving medium reduces the chance of devascularization occurring in the piece of tissue. The time between obtaining the piece of tissue from one part of the body and grafting the tissue in another part of the body preferably ranges from 15 minutes to 60 minutes.

The method is useful for any case where autotransplantation of tissue is appropriate, e.g., for correcting defects in the urinary tract or in the vascular system or in other sites of the body or for other purposes. As indicated above, an instance of autotransplantation involving the urinary tract, is for the repair of hypospadias, especially for the repair of hypospadias with extragenital tissue, e.g., non-hair bearing skin tissue, bladder mucosa tissue and buccal mucosa tissue. One instance of autotransplantation involving the vascular system is to bypass an occlusive lesion of the superficial femoral, popliteal, or tibial arteries. In such case, autogenous vein (usually the greater saphenous) is anastomosed end-to-side to the occluded vessel above and below the occlusion. Another case of autotransplantation is for skin grafts because of burns or other massive skin loss where healthy skin is grafted in the area of skin loss. Still another case of autotransplantation is parathyroid autotransplantation in the treatment of patients with hypercalcemia due to secondary hyperplasia. In this case, parathyroid tissue is removed from the neck and some of it is placed in a muscle pocket in the forearm where tissue can be easily identified if hypercalcemia recurs.

In an instance of special importance, the method of autotransplantation herein is for repair of hypospadias and comprises obtaining tissue from the mouth of a male human affected with hypospadias, and particularly a piece of buccal mucosa, preserving the piece of tissue by contacting it with a tissue preserving medium (to keep it moist), and grafting the piece of tissue to reconstruct the hypospadias. Preferably the piece of tissue (buccal mucosal tissue) which is removed for grafting is rectangular in shape and is formed into a tube shape and is grafted to native urethra in said tube shape (positioned axially inside the penis) to reconstruct the hypospadias. Supporting (and stabilizing) of the graft tissue, rotation for debriding and tube shape formation is preferably effected using a graft tubularization apparatus as described in Provisional Patent application Ser. No. 60/027,915 and in the corresponding non-provisional patent application filed concurrently herewith (CRF D-1972A) of the inventors herein entitled "Method and Apparatus for Support and Tubularization of Surgical Grafts", the disclosures of which are incorporated herein by reference.

Suturing in the autotransplantation methods herein is preferably carried out with a microsurgical suture needle as described in Provisional application Ser. No. 60/027,910 and in the corresponding non-provisional patent application filed concurrently herewith (CRF D-1973A) of the inventors herein, the disclosures of which are incorporated herein by reference. The use of a microsurgical suture needle in the repair of hypospadias in the method of the second embodiment herein reduces the chance for urethrocutaneous fistulas to occur after the reconstruction is completed.

The tissue preserving medium for use in the second embodiment herein is preferably an aqueous solution which contains two kinds of antibiotics, namely at least one antibiotic which is a p-lactam antibiotic and at least one antibiotic which is an aminoglycoside antibiotic. The antibiotics reduce the chance for infection occurring in the graft tissue and thereby reduce the chance of occurrence of urethrocutaneous fistulas occurring after the reconstruction is completed in the repair of hypospadias in the method of the second embodiment herein. Preferably, the tissue preserving medium for the second embodiment herein is that of the first embodiment herein. Preferably, the tissue preserving medium for the second embodiment is buffered to a pH ranging from 7.0 to 7.8. The buffering protects against acid formation due to anaerobic respiration leading to tissue death. The tissue preserving medium for the second embodiment, very preferably, is Pedic-Uro MHR™ medium as described above. Other tissue preserving media include that having the same composition as the first embodiment herein except with less than 125 units/ml penicillin-G, e.g., 75–110 units/ml penicillin-G. Still other tissue preserving media for use in the second embodiment herein include the "medical solutions" described in Lindstrom et al U.S. Pat. No. 5,104,787 and tissue preserving solutions described, for example, in Brockbank U.S. Pat. No. 5,110,772; Bretan U.S. Pat. No. 4,920,044; and Belzyer et al U.S. Pat. No. 4,873,230.

The embodiments of the invention described above are illustrated in the following working examples:

EXAMPLE I

A tissue preserving medium is made up having the following composition:

102 mM NaCl 4.7 mM KCl 0.2 mM $MgSO_4.7H_2O$ 2 mM $CaCl_2.2H_2O$ 0.5 mM $NaH_2PO_4$ 2.8 mM glucose 21 mM Na lactate 0.4 mM Na pyruvate 0.02 mM phenol red 0.2 mM L-glutamine 4 mM sodium bicarbonate 150 units/ml penicillin-G 50 μg/ml streptomycin sulfate 21 mM HEPES water The water is distilled water. The sodium bicarbonate is sodium bicarbonate without protein, i.e., which is entirely free of protein. The HEPES buffers the medium to a pH of about 7.4.

The composition is made up by buying composition the same except for containing 100 units/ml of penicillin-G and no HEPES (commercially available from Life Technologies of Grand Island, New York and from Irving Scientific of Sweden) and admixing into it 50 units/ml penicillin-G and crystals of HEPES.

EXAMPLE II

The patient is a newborn boy with hypospadias and particularly with a urethral opening on the underside of the penis at a point proximal to the distal end of the penis.

A piece of tissue for grafting is obtained from the patient as follows: The inside of a cheek is sterilized by the application of betadine and isolated sterilely. A surgical knife with a 15 degree blade is used to remove from the sterilized isolated inner portion of the cheek, a generally rectangular surface flat piece of buccal mucosal tissue of dimensions 2 by 4 cm by 1 to 2 mm thick.

The removed piece of buccal mucosa tissue is quickly (about 1 second) transferred with tissue forceps into a well of a graft tubularization apparatus that is filled with tissue preserving medium of composition prepared in Example I and is maintained submerged in said tissue preserving medium. The graft tubularization apparatus (GTA) is of structure as described in Provisional application Ser. No. 60/027,915 and the nonprovisional patent application (CRF D-1972A) filed concurrently herewith titled "Method and Apparatus for Support and Tubularization of Surgical Grafts" of the inventors herein, the disclosures of which are incorporated herein by reference.

The tissue piece is initially suspended on the graft tubularization apparatus in contact with the tissue preserving medium in generally flat horizontal orientation as described in Ser. No. 60/027,915 and the related non-provisional patent application (CRF D-1972A) and after debriding is wrapped around a mandrel which is inserted into mandrel holes in the graft tubularization apparatus to form the tissue piece into tubular shape with the long sides of the rectangle being brought into butting relation as described in said applications. The tissue piece is removed from contact with tissue preserving medium in the well of the GTA for forming into tubular shape and is kept moist by irrigation with the tissue preserving medium using a 10 cc syringe during tube shape formation.

The tubularization is completed by suturing the long sides together using 9-O vicryl suture material to hold the tube together. The suturing is carried out with a non-traumatic microsurgical needle, the structure of which is described in Provisional Patent application Ser. No. 60/027,910 and in the non-provisional patent application (CRF D-1973A) filed concurrently herewith titled "Microsurgical Suture Needle" of the inventors herein, the disclosures of which are incorporated herein by reference. The tissue is kept moist by irrigation with tissue preserving medium using a 10 cc syringe during the suturing.

The time from removal of the piece of buccal mucosa tissue to completion of tubularization is about 30 minutes.

The penis is then reconstructed as follows: The penis is cut open axially using a scalpel and the tube shaped piece of graft material is removed from the graft tubularization apparatus and is positioned axially in the opened penis so that one end contacts native urethra, and after the insertion of a catheter through the passage of the tube of the graft tissue and into the native urethra, is anastomosed to the native urethra by suturing with 9-O vicryl suture material to create a new urethra meatus whereupon the penis is sutured together along its length with said microsurgical suture needle to complete the reconstruction procedure. During the course of the reconstruction, the graft tissue is kept moist and viable by irrigation with the tissue preserving medium using a 10 cc syringe. The sutures dissolve. The catheter bridging the anastomosis is removed after seven days and the patency of anastomosis is maintained.

Variations will be evident to those skilled in the art. Therefore, the scope of the invention is intended to be defined by the claims.

What is claimed is:

1. A tissue preserving medium in the form of a solution, consisting essentially of (a) 80–120 mM NaCl, (b) 3–6 mM KCl, (c) 0.1–0.3 mM $MgSO_4 \cdot 7H_2O$, (d) 1–3 mM $CaCl_2 \cdot 2H_2O$, (e) 0.2–0.6 mM $NaH_2PO_4$, (f) 1.5–4 mM glucose, (g) 15–25 mM Na lactate, (h) 0.2–0.6 mM Na pyruvate, (i) 0.01–0.05 mM phenol red, (j) 0.1–0.4 mM L-glutamine, (k) 2–35 mM sodium bicarbonate, (1) 125–200 units/ml penicillin-G, (m) 40–60 $\mu$/ml streptomycin sulfate, (n) vehicle consistent with tissue preservation; said medium having a pH ranging from 7.0–7.8.

2. The tissue preserving medium of claim 1 which is buffered to a pH ranging from 7.0–7.8.

3. The tissue preserving medium of claim 2 wherein the vehicle is aqueous HEPES solution.

4. The tissue preserving medium of claim 1 wherein said vehicle is selected from the group consisting of aqueous HEPES solution, Ringer's solution and saline.

5. The tissue preserving medium of claim 1 having the following composition: 102 mM NaCl, 4.7 mM KCl, 0.2 mM $MgSO_4 \cdot 7H_2O$, 2 mM $CaCl_2 \cdot 2H_2O$, 0.5 mM $NaH_2PO_4$, 2.8 mM glucose, 21 mM Na lactate, 0.4 mM Na pyruvate, 0.02 mM phenol red, 0.2 mM L-glutamine, 4 mM sodium bicarbonate, 150 units/ml penicillin-G, 50g/ml streptomycin sulfate, 21 mM HEPES, and water.

* * * * *